(12) United States Patent
Wei

(10) Patent No.: US 7,039,561 B2
(45) Date of Patent: May 2, 2006

(54) OUTLIER REJECTION METHOD IN AN AUTOMATIC CLINICAL ANALYZER

(75) Inventor: Tie Quan Wei, Bear, DE (US)

(73) Assignee: Dade Behring Inc., Deerfield, IL (US)

( * ) Notice: Subject to any disclaimer, the term of this patent is extended or adjusted under 35 U.S.C. 154(b) by 0 days.

(21) Appl. No.: 10/865,081

(22) Filed: Jun. 10, 2004

(65) Prior Publication Data

US 2005/0288908 A1    Dec. 29, 2005

(51) Int. Cl.
G06F 15/00    (2006.01)
H03F 1/26     (2006.01)
H04B 15/00    (2006.01)

(52) U.S. Cl. .................. 702/191; 702/189; 702/190

(58) Field of Classification Search ........ 702/191, 702/179–181; 356/319–326
See application file for complete search history.

(56) References Cited

U.S. PATENT DOCUMENTS

| 4,627,014 A | 12/1986 | Lo et al. ................. 364/571 |
| 4,744,657 A | 5/1988 | Aralis et al. ............... 356/319 |
| 4,782,456 A | 11/1988 | Poussier et al. ............ 364/574 |
| 5,046,846 A | 9/1991 | Ray et al. .................. 356/326 |
| 5,083,283 A | 1/1992 | Imai et al. ................. 364/497 |
| 5,369,578 A | 11/1994 | Roscoe et al. ............. 364/422 |
| 5,552,997 A | 9/1996 | Massart ................. 364/571.01 |
| 6,341,257 B1 | 1/2002 | Haaland ..................... 702/27 |
| 6,560,546 B1 * | 5/2003 | Shenk et al. ................. 702/30 |
| 6,629,090 B1 | 9/2003 | Tsuda et al. ................. 706/47 |
| 6,763,308 B1 * | 7/2004 | Chu et al. ................... 702/19 |
| 2002/0094535 A1 | 7/2002 | Nadon et al. ................. 435/6 |

* cited by examiner

*Primary Examiner*—John Barlow
*Assistant Examiner*—Sujoy Kundu
(74) *Attorney, Agent, or Firm*—Leland K. Jordan (57) ABSTRACT

Automatically rejecting outlier measurements in an analytical method employing multiple photometric values by determining the photometric value that is involved in the pair of photometric values having the greatest variance between individual mean rates and the mean rate of all of the multiple photometric values.

3 Claims, 11 Drawing Sheets

OUTLIER REJECTION METHOD IN AN AUTOMATIC CLINICAL ANALYZER

FIELD OF THE INVENTION

The present invention relates to a method for automatically processing a patient's biological fluids such as urine, blood serum, plasma, cerebrospinal fluid and the like. In particular, the present invention provides a method for identifying outlier data points in reaction rate measurements within an automatic clinical analyzer.

BACKGROUND OF THE INVENTION

Various types of tests related to patient diagnosis and therapy can be performed by analysis of a sample of a patient's infection, bodily fluid or abscess for an analyte of interest. Patient samples are typically placed in closed sample tubes, the tubes transported to a clinical laboratory, placed into racks on an automated clinical analyzer and sample is extracted from the tubes. Subsequently, samples are combined in reaction vessels with various reagents extracted from reagent containers; the mixture is possibly incubated before being analyzed to aid in treatment of the patient. Interrogating measurements, turbidimetric or fluorometric or the like, may be employed to ascertain reaction rate values from which the amount of analyte in the sample may be determined using well-known calibration techniques. Herein, reagents, quality control, and calibration solutions may be referred to as analytical solutions.

Automated clinical analyzers improve operating efficiency by providing results more rapidly while minimizing operator or technician error. Due to increasing demands on clinical laboratories regarding assay accuracy, in particular for assays employing smaller patient samples, error sources continually need to be eliminated.

In many clinical assays, an immunochemical reaction between a soluble antigen and a bivalent or polyvalent antibody generates large groups of molecules which scatter light measurable by photometric sensors. The time profile of such reactions very frequently corresponds to the general kinetic profile of successive first order reactions from which concentration-dependent measurement signals can be determined. Such reactions are generally governed by thermodynamic factors and thus random variations in constitution or physical state of the analytical solutions employed, as well as random variations in the physical state of the analytical devices employed, may cause random variation in the measurement signals obtained. Such random variations are different from assay drift which derives from systematic changes that can be detected using well known system control procedures.

A known source of errors in clinical analyzers is the appearance of such random variations, known as outliers, in measurement data values that fall well outside established ranges or predictable limits, and therefore usually of limited value in analytical determinations.

SUMMARY OF THE INVENTION

The present invention provides a method for rejecting outlier measurements in an analytical method employing multiple photometric values by identifying and rejecting the photometric value that forms one of the pair of photometric values having the greatest variance between all possible individual mean rates between the totality of multiple photometric values and the mean rate of all of the multiple photometric values. Advantages in analytical accuracy through error reduction are thusly achieved.

BRIEF DESCRIPTION OF THE DRAWINGS

The invention will be more fully understood from the following detailed description thereof taken in connection with the accompanying drawings which form a part of this application and in which.

DETAILED DESCRIPTION OF THE INVENTION

Figure 1:
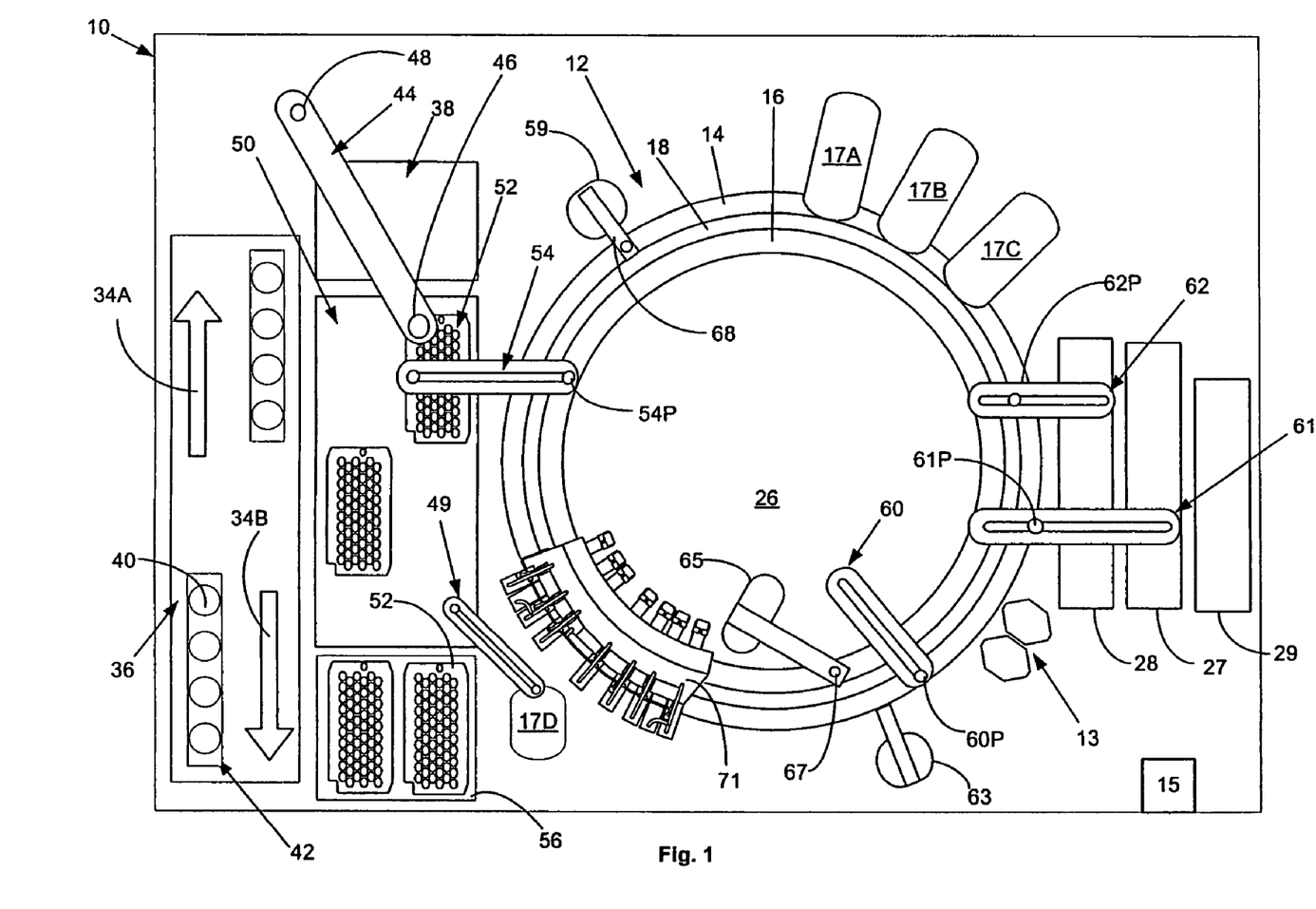
FIG. 1 is a schematic plan view of an automated analyzer in which the present invention may be employed to advantage.
Figure 2:
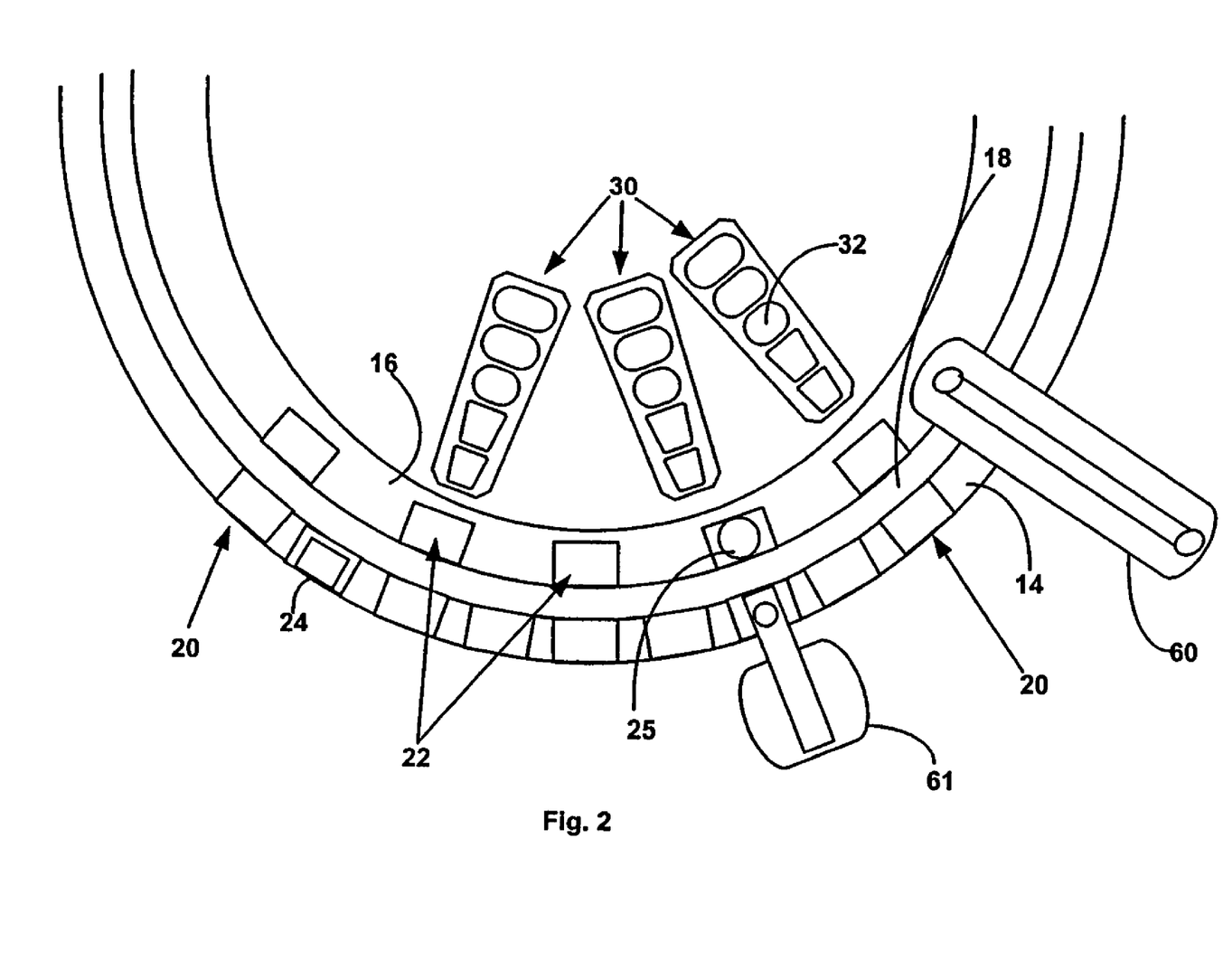
FIG. 2 is an enlarged schematic plan view of a portion of the analyzer of FIG. 1.

FIG. 1, taken with FIG. 2, shows schematically the elements of an automatic chemical analyzer 10 in which the present invention may be advantageously practiced, and in which analyzer 10 comprises a reaction carousel 12 supporting an outer cuvette carousel 14 having cuvette ports 20 formed therein and an inner cuvette carousel 16 having vessel ports 22 formed therein, the outer cuvette carousel 14 and inner cuvette carousel 16 being separated by a open groove 18. Cuvette ports 20 are adapted to receive a plurality of reaction cuvettes 24 like disclosed in co-pending application Ser. No. 09/949,132 assigned to the assignee of the present invention and containing various reagents and sample liquids for conventional clinical and immunoassay assays while vessel ports 22 are adapted to receive a plurality of reaction vessels 25 that contain specialized reagents for ultra-high sensitivity luminescent immunoassays. Reaction carousel 12 is rotatable using stepwise movements in a constant direction, the stepwise movements being separated by a constant dwell time during which carousel 12 is maintained stationary and computer controlled assay operational devices 13, such as sensors, reagent add stations, mixing stations and the like, operate as needed on an assay mixture contained within cuvettes 24 and reaction vessels 25.

Analyzer 10 is controlled by software executed by computer-based operating control system 15 using computer programs written in a machine language like that on the Dimension® clinical chemistry analyzer sold by Dade Behring Inc, of Deerfield, Ill., and widely used by those skilled in the art of computer-based electromechanical control programming. Operating system 15 also executes application software programs for performing assays conducted by various analyzing units 17A, 17B, 17C and 17D located proximate outer cuvette carousel 14. It is advantageous that analyzing unit 17A be a conventional luminometer or a chemiluminometer configured to allow analyzer 10 to perform luminescent oxygen channeling immunoassays ("LOCI"). LOCI assays provide significant advantage over many conventional immunoassays because they are highly specific and can be performed without time-consuming separation steps. A full description of the LOCI method can be found in U.S. Pat. No. 5,340,716.

Figure 3:
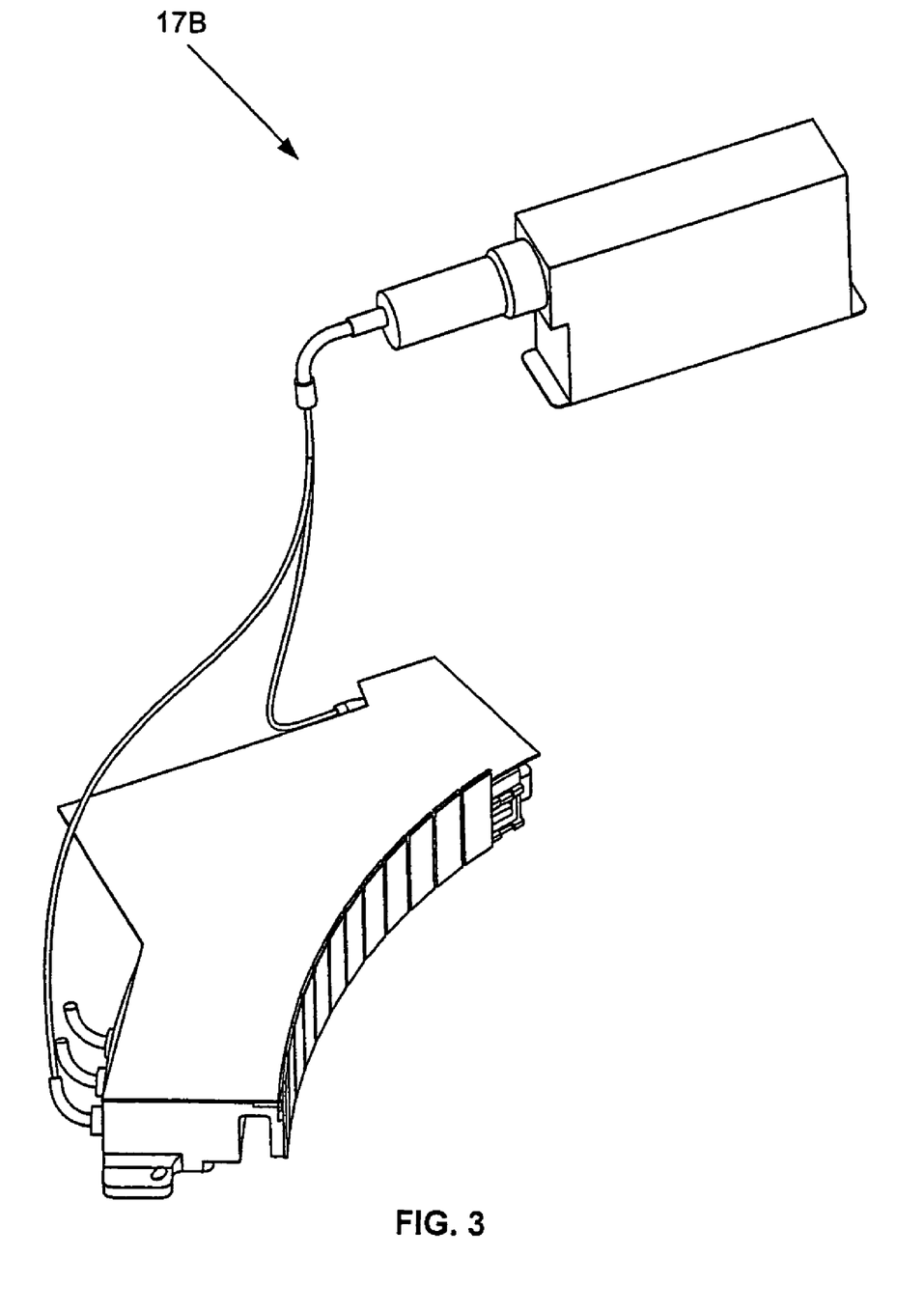
FIG. 3 is an analyzing unit useful in the analyzer of FIG. 1.
Figure 4:
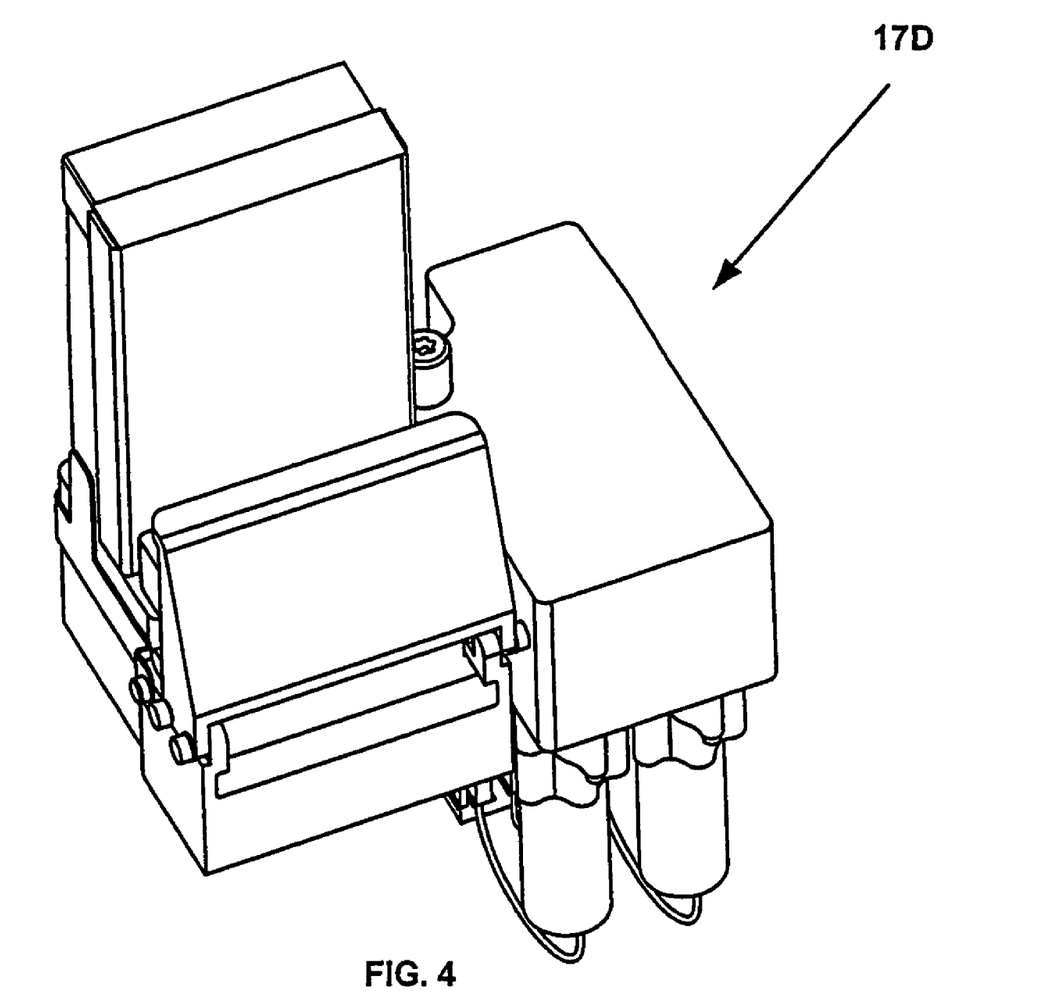
FIG. 4 is an integrated measuring sensor useful in the analyzing unit of FIG. 2B.

Remaining analyzing units 17B and 17C are preferably adapted to perform different, non-luminescence based analyses in order to optimize and diversify the capabilities of analyzer 10. For example, analyzing unit 17B may include a photometer or a turbidometer like seen in FIG. 3. A suitable photometer is used as part of the Dimension® clinical chemistry analyzer manufactured and sold by Dade Behring Inc. of Deerfield, Ill. Analyzing unit 17C may include yet a different type of detector, such as a nephelometer. Furthermore, analyzing unit 17D preferably is yet another, different type of detector, such as an ion selective electrode (ISE) measuring unit 17D like seen in FIG. 4 using an ISE integrated measuring sensor 19 like seen in FIG. 2C. ISE integrated measuring device 19 is like that described in U.S. Pat. No. 5,964,994.

Figure 6:
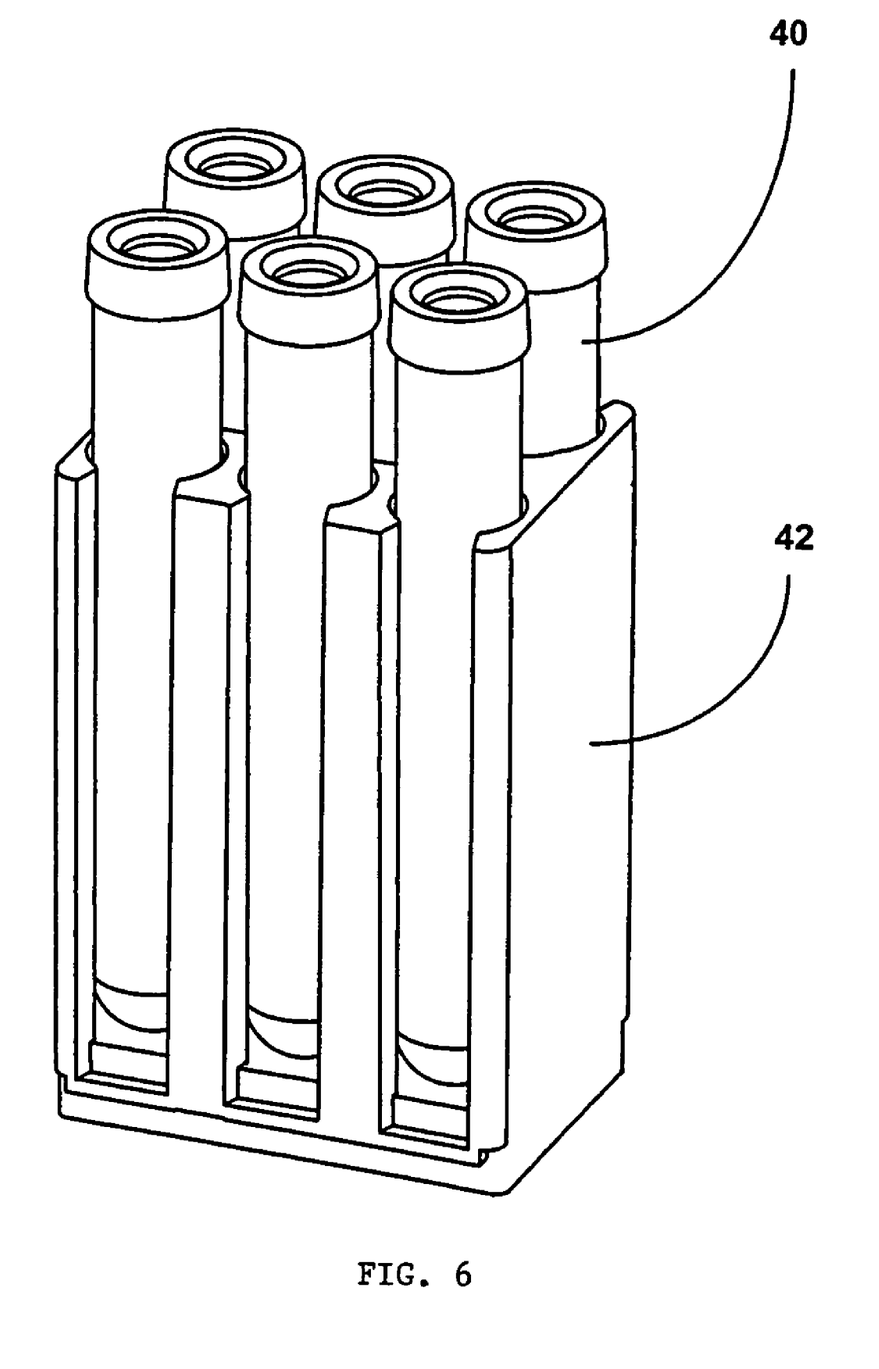
FIG. 6 is a perspective view of a sample tube and sample tube rack useful in performing the present invention.

A bi-directional incoming and outgoing sample tube transport system 36 having input lane 34A and output lane 34B transports incoming individual sample tubes 40 containing liquid specimens to be tested and mounted in sample tube racks 42, as seen in FIG. 6, into the sampling arc of a liquid sampling arm 44. Liquid specimens contained in sample tubes 40 are identified by value a conventional one dimension bar code indicia placed thereon with a conventional bar code reader to determine, among other items, a patient's identity, tests to be performed, if a sample aliquot is to be retained within analyzer 10 and if so, for what period of time, and the like.

Figure 5:
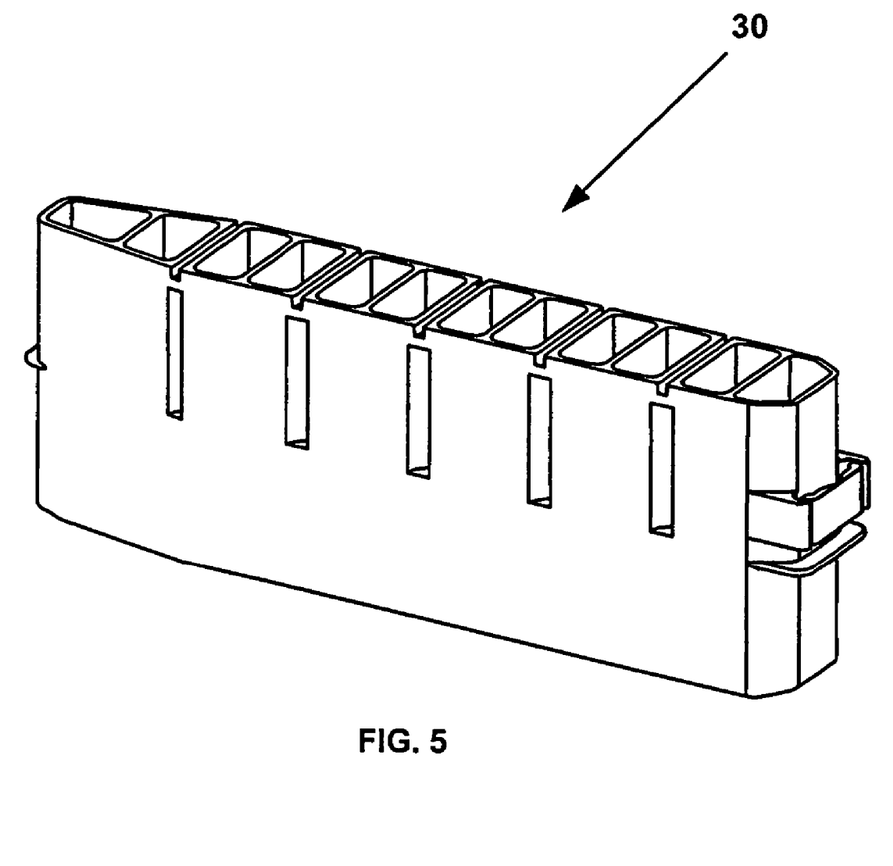
FIG. 5 is a perspective view of a reagent container useful in the analyzer of FIG. 1 and useful in performing the present invention.
Figure 7A:
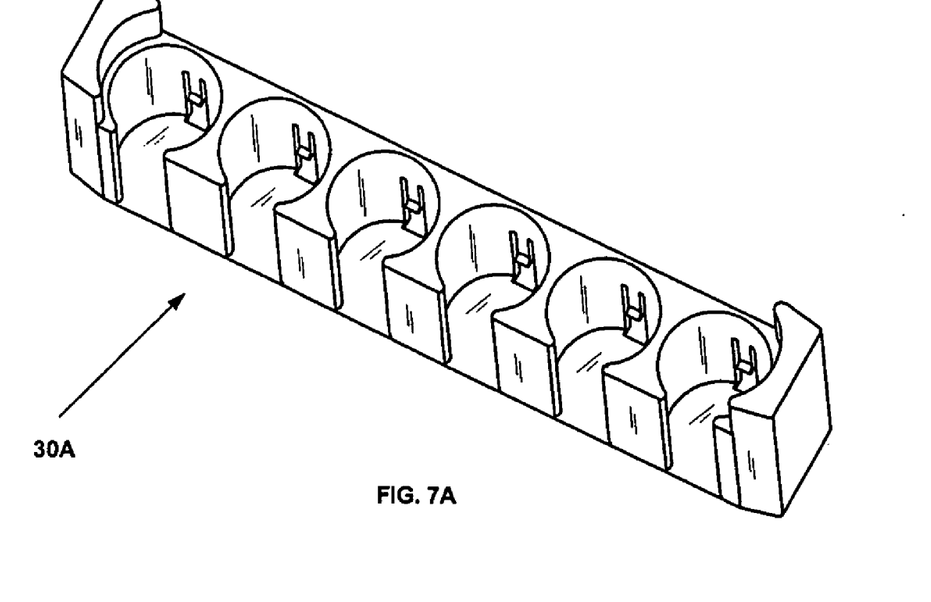
FIG. 7A is a perspective view of a vial container carrier useful in the analyzer of FIG. 1 and useful in performing the present invention.
Figure 7B:
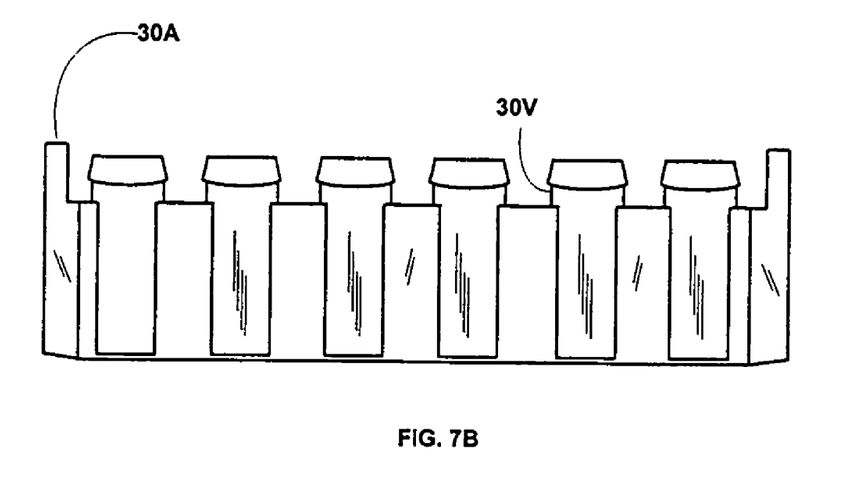
FIG. 7B is a elevation view of the vial container of FIG. 7A.

Temperature-controlled reagent storage areas 26, 27 and 28 store a plurality of multi-compartment elongate liquid chemical reagent containers 30 like that illustrated in FIG. 5, containing reagents necessary to perform a given assay within a number of wells 32, each well containing as much as 3.4 mL of a given reagent. FIGS. 7A and 7B show a liquid chemical calibration vial container carrier 30A containing calibration solutions of known analyte concentrations in calibration solution vials 30V, the solutions being to conduct well-know calibration and quality control procedures within analyzer 10.

Figure 8:
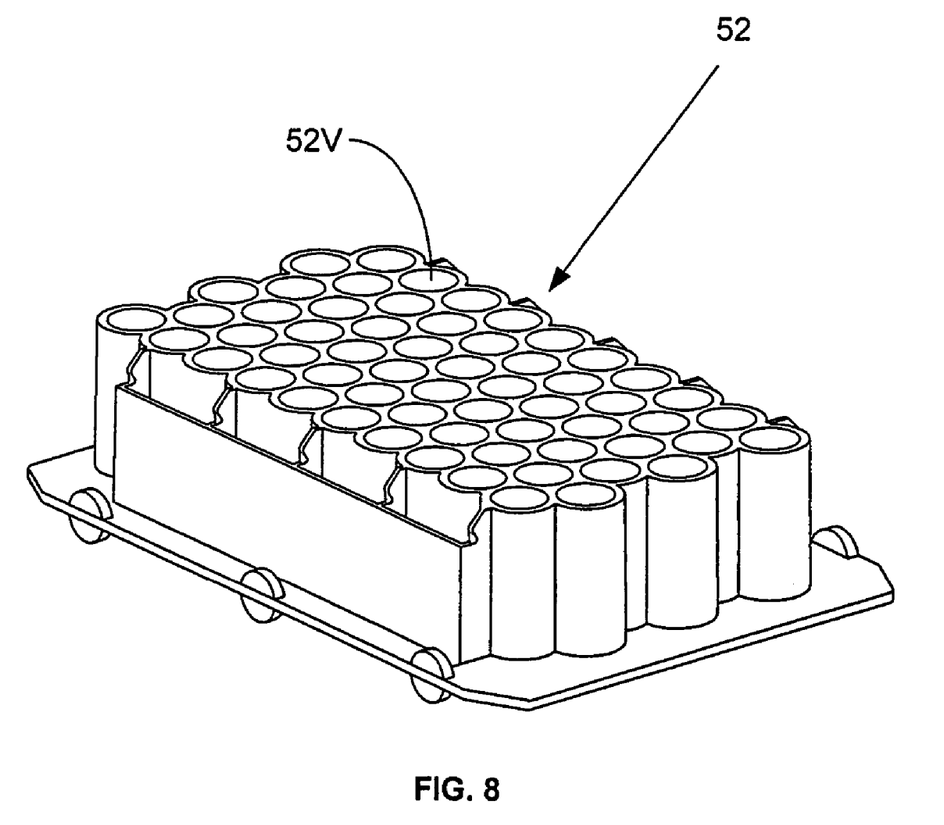
FIG. 8 illustrates an aliquot vessel array useful in the analyzer of FIG. 1 and useful in performing the present invention.

Sampling arm 44 supports a liquid sampling probe 46 mounted to a rotatable shaft 48 so that movement of sampling arm 44 describes an arc intersecting the sample tube transport system 36 and an aliquot vessel array transport system 50, as seen in FIG. 5A. Sampling arm 44 is operable to aspirate liquid sample from sample tubes 40 and to dispense an aliquot sample into one or more of a plurality of vessels 52V in aliquot vessel array 52, as seen in FIG. 8, depending on the quantity of sample required to perform the requisite assays and to provide for a sample aliquot to be retained by analyzer 10 within environmental chamber 38.

Aliquot vessel array transport system 50 comprises an aliquot vessel array storage and dispense module 56 and a number of linear drive motors 58 adapted to bi-directionally translate aliquot vessel arrays 52 within a number of aliquot vessel array tracks 57 below a sample aspiration and dispense arm 54 located proximate reaction carousel 12. Sample aspiration and dispense arm 54 is controlled by operating system 15 and is adapted to aspirate a controlled amount of sample from individual vessels 52V positioned at a sampling location within a track 57 using a conventional liquid probe 54P and then liquid probe 54P is shuttled to a dispensing location where an appropriate amount of aspirated sample is dispensed into one or more cuvettes 24 in cuvette ports 20 for testing by analyzer 10 for one or more analytes. After sample has been dispensed into reaction cuvettes 24, conventional transfer means move aliquot vessel arrays 52 as required between aliquot vessel array transport system 50, environmental chamber 38 and a disposal area, not shown.

A number of reagent aspiration and dispense arms 60, 61 and 62 each comprising at least one conventional liquid reagent probe, 60P, 61P and 62P, respectively, are independently mounted and translatable between reagent storage areas 26, 27 and 28, respectively. Probes 60P, 61P and 62P are conventional mechanisms for aspirating reagents required to conduct specified assays at a reagenting location from wells 32 in an appropriate reagent container 30, the probes 60P, 61P and 62P subsequently being shuttled to a reagent dispensing location where reagent(s) are dispensed into reaction cuvettes 24. Probes 60P, 61P and 62P are also used for aspirating calibration and control solutions from calibration solution vials 30V as required to conduct calibration and control procedures necessary to ensure proper operation of analyzer 10, the probes 60P, 61P and 62P subsequently being shuttled to a calibration solution dispensing location where solutions(s) are dispensed into reaction cuvettes 24 and analyzed by analyzing means 17A–D.

Reaction cuvette load station 61 and reaction vessel load station 63 are respectively positioned proximate outer cuvette carousel 14 and inner vessel carousel 16 and are adapted to load reaction cuvettes 24 into cuvette ports 20 sideways as described later and reaction vessels 25 into vessel ports 22 using for example a translatable robotic arm 65. In operation, used cuvettes 24 in which an assay has been finally conducted, are washed and dried in a wash station 67 like disclosed in co-pending application Ser. No. 10/623,360 assigned to the assignee of the present invention. Subsequent assays are conducted in cleaned used cuvettes 24 unless dictated otherwise for reasons like disclosed in co-pending application Ser. No. 10/318,804 assigned to the assignee of the present invention. Cuvette unload station 59 is adapted to remove unusable reaction cuvettes 24 from cuvette ports 20 again using a translatable robotic arm 65 like seen on load stations 61 and 63.

Figure 9:
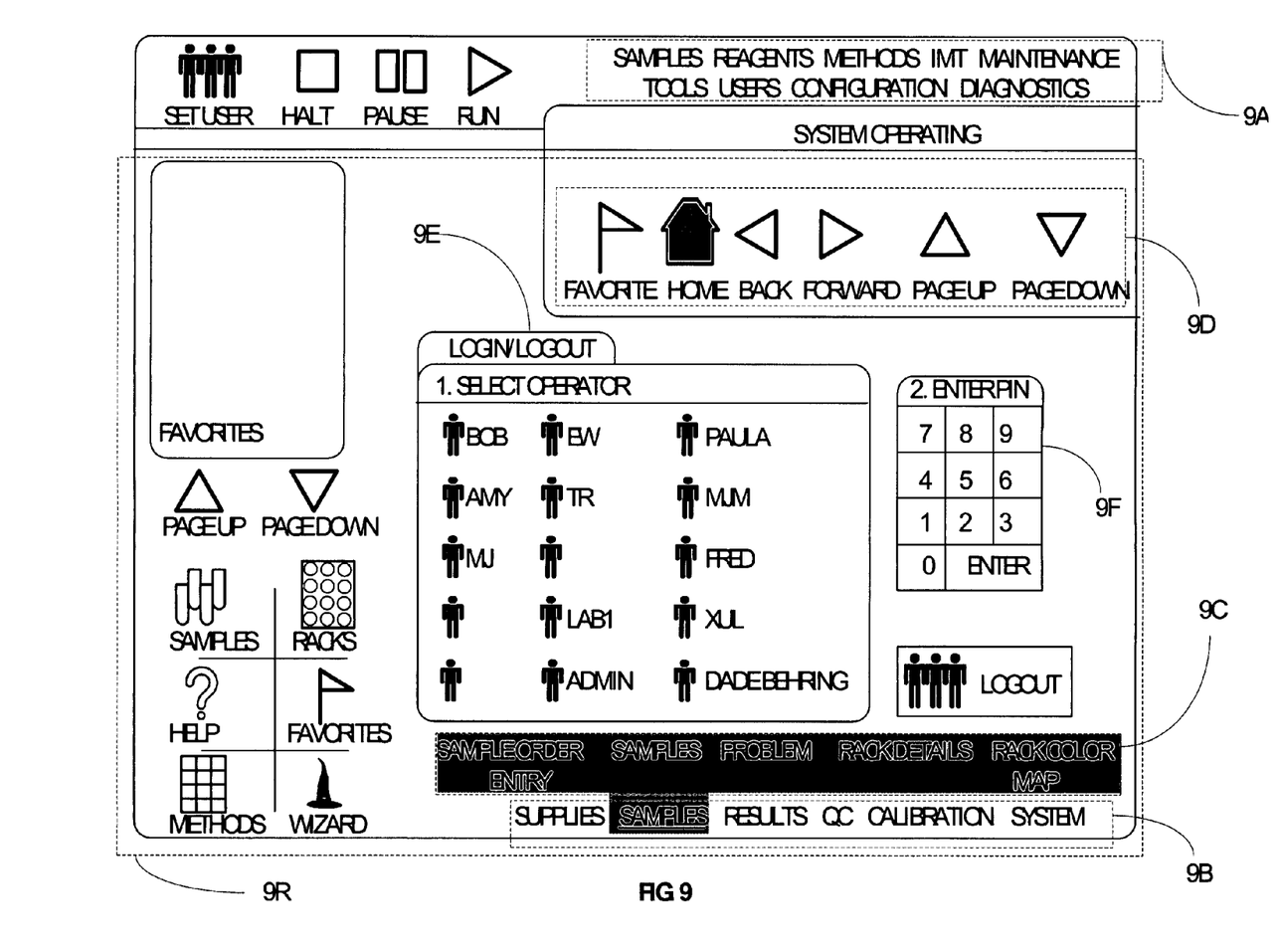
FIG. 9 illustrates a display screen associated with operation of the analyzer of FIG. 1.

FIG. 9 is an example of viewing screen 15S in which the routine operational information occupies the lower, greater than 90% of screen 15S, identified as 9R and this information is easily accessed using only the tab rows 9B and 9C at the bottom of screen 15S and the Home/Back/Forward buttons 9D. About 10% of screen 15S, indicated by 9A, contains advanced operational information. Computer 15 is programmed to structure screen 15S on an operator specific basis so that a routine user cannot stumble into complexity that they are unable to handle. This structuring has implications in documentation and training programs, and also makes it much easier to train an operator to accomplish the essential functions required to maintain continuous throughput in analyzer 10, without needing to provide extensive overall operational knowledge. A login/Logout area 9E may be seen in FIG. 9 where both routine operators and qualified technicians having been trained in non-routine, advanced aspects of operating analyzer 10 may gain access to linked screens after sequentially touching a Personal Information Number in area 9F. Only a relatively few linked information screens, shown shaded, are in 90, about 5 in each category in 9B. Active buttons in area 9R are touch-activated. For convenience, dashed lines are used in FIG. 9 to indicate areas within screen 15S.

From the preceding description of analyzer 10, it is clear to one skilled in the art that the capabilities of analyzer 10 under the control of operating system 15 include the ability to automatically ascertain reaction rate values in turbidimetric or fluorometric assays from which the amount of analyte in the sample may be determined using well-known calibration techniques. The present invention improves the capabilities of analyzer 10 by adding the capability to automatically reject outlier measurements in an analytical method employing multiple photometric values thereby reducing the possibility of measurement errors and increasing analytical accuracy.

Figure 10:
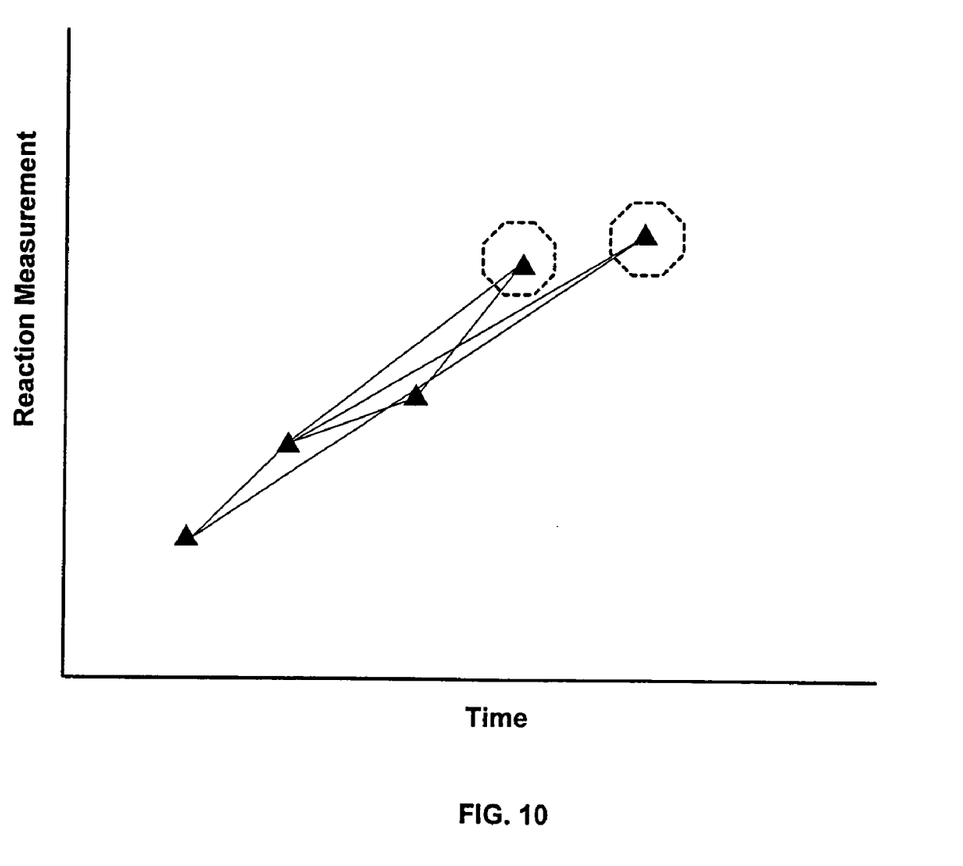
FIG. 10 illustrates a first instance in which the present invention may be employed and reaction measurement values are evenly distributed throughout the duration of an analysis; and, FIG. 11 illustrates a second instance in which the present invention may be employed and reaction measurement values are unevenly distributed throughout the duration of an analysis.
Figure 11:
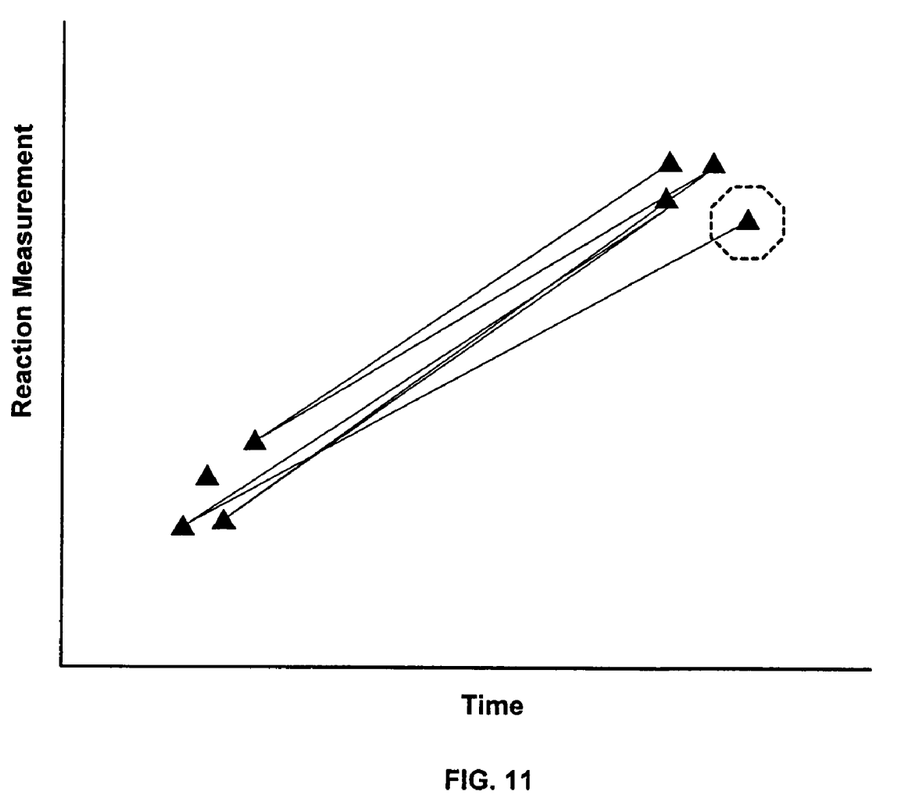

FIG. 10 illustrates a first instance in which reaction measurement values by, for example analyzing unit 17B, are evenly distributed throughout the duration of the analysis. Five individual values are shown and a number of them are connected to indicate that every possible combination of two data measurements or values will be evaluated in the outlier rejection scheme of the present invention. The number of values is not critical as a greater number might normally be obtained; only five are shown in FIG. 10 for purposes of simplicity, however as seen in FIG. 11, in a second instance in which reaction measurement values are unevenly distributed throughout the duration of the analysis, n may be 10 or more.

The first step in the outlier rejection scheme is to determine the maximum number, N, of different signal data value pairs, each formed by two different signal value data measurements, identified as $S_i$ for example, that may be identified without duplicating any single value data measurement pair formed from the totality of different signal values. Next calculate the rate of measurement change, say $R_{ij}$ for the Signals $S_i$ and $S_j$ between all different data pairs. N may be found using Formula 1 where n=the number of measurement Signals.

Formula 1 $N = n!/2(n-2)!$

The second step in the outlier rejection scheme is to calculate the arithmetic mean rate, herein MR, from the totality of individual data measurement pairs, $RP_{ij}$ for i and j=1 to N for all N of different Signal pairs. Obviously a pair cannot be formed if I=j throughout this scheme.

The third step in the outlier rejection scheme is to calculate the variance between the mean rate, MR, and the individual rates, $R_{ij}$ for i and j=1 to N for all N of different Signal pairs, using Formula 2:

Formula 2 Variance=$[MR-R_{ij}]^2$, for i=1 to N for all N of the different signal pairs. The square root of the sum of variances between the mean rate, MR, and the rates of change $R_{ij}$, for i and j=1 to N, is calculated and is referred to herein as SSM.

The fourth step in the outlier rejection scheme is to identify the individual rate having the maximum variance between the mean rate, MR, and the rates of change $R_{ij}$, for i and j=1 to N. For the sake of identification, identify the two individual Signals as $S_j$ and $S_k$, $S_j$ and $S_k$ forming the Signal pair having the maximum variance between the mean rate, MR, and the rates of change $R_{ij}$ for i and j=1 to N.

The fifth step in the outlier rejection scheme is to recalculate the mean rate of the rates of change $R_{ij}$ for i and j=1 to N, except that the individual Signal $S_j$ is excluded. For the sake of identification, this recalculated mean rate is identified as $MR_k$.

The sixth step in the outlier rejection scheme is to recalculate the mean rate of the rates of change $R_{ij}$ for i and j=1 to N, except that the individual Signal $S_k$ is excluded. For the sake of identification, this recalculated mean rate is identified as $MR_j$.

The seventh step in the outlier rejection scheme is to calculate the variance=$[MR-R_{ij}]^2$, for i=1 to N for all N of the different signal pairs, except that the individual signal $S_j$ is excluded. The square root of the sum of the variances between the mean rate, $MR_k$, and the rates of change $R_{ij}$, for i and j=1 to N, except that the individual signal $S_j$ is excluded, is calculated and is referred as $SSM_k$.

The seventh step in the outlier rejection scheme is to calculate the variance=$[MR-R_{ij}]^2$, for i=1 to N for all N of the different signal pairs, except that the individual Signal $S_j$ is excluded. The square root of the sum of the variances between the mean rate, $MR_j$, and the rates of change $R_{ij}$, for i and j=1 to N, except that the individual signal $S_k$ is excluded, is calculated and is referred as $SSM_j$.

The final step in the outlier rejection scheme is to determine the larger of the two values, $SSM_k$ and $SSM_j$, both being less than SSM. The comparison between the two values, $SSM_k$ and $SSM_j$ determines which of the individual signals $S_k$ or $S_j$ is to be rejected. That is, if $SSM_k$ is greater than $SSM_j$, then $S_k$ is to be rejected. Otherwise, $S_j$ is to be rejected. $MR_j$ is to be reported If $S_k$ is rejected, otherwise, $MR_k$ is to be reported.

Steps four to seven can be reiterated to reject more than one outlier signal data point.

A simplified example of the outlier rejection scheme can be illustrated using experimental data like that shown in Table I.

TABLE I

| Data Measurement | Elapsed Time | Relative Signal |
|---|---|---|
| $S_1$ | 13.6 | 300 |
| $S_2$ | 29.7 | 330 |
| $S_3$ | 49.8 | 489 |
| $S_4$ | 62.1 | 556 |

Per Formula 1, N should equal 6 since there are five data measurements and these may be identified as presented in Table II.

TABLE II

| Data Measurement Pair | Calculated Rate of Measurement Change |
|---|---|
| RP2,1 | 110 |
| RP3,1 | 313 |
| RP4,1 | 316 |
| RP3,2 | 475 |
| RP4,2 | 418 |
| RP4,3 | 325 |
| MeanRate | 326 |

As explained above, next the two individual Signals having the maximum variance between the mean rate, MR, and the rates of change $R_{ij}$ is determined as illustrated in Table III.

TABLE III

| Data Measurement Pair | Variance From Mean |
|---|---|
| $RP_{2,1}$ | 46767 |
| $RP_{3,1}$ | 179 |
| $RP_{4,1}$ | 106 |
| $RP_{3,2}$ | 22245 |
| $RP_{4,2}$ | 8472 |
| $RP_{4,3}$ | 2 |
| SSM | 279 |

From this variance calculation, and in accord with the present invention, the Signal pair $RP_{2,1}$ has an "outlier" and either data measurement 2 or 1 is the outlier to be identified. In order to ascertain which data measurement 2 or 1 is the unwanted outlier. As explained in the fifth and sixth steps above, the present invention recalculates the mean rate of the rates of change $R_{ij}$ for i and j=1 to N, except that the individual Signal $S_2$ is excluded as illustrated in Table IV and this process is repeated except that the individual Signal $S_1$ is excluded, as illustrated in Table V.

TABLE IV

| Data Measurement Pair Without $R_4$ | Rate of Measurement Change |
|---|---|
| $RP_{3,1}$ | 313 |
| $RP_{4,1}$ | 316 |
| $RP_{4,3}$ | 325 |
| $MR_1$ | 318 |
| $SSM_1$ | 9 |

TABLE V

| Data Measurement Pair Without $R_4$ | Rate of Measurement Change |
|---|---|
| $RP_{3,2}$ | 475 |
| $RP_{4,2}$ | 418 |
| $RP_{4,3}$ | 325 |
| $MR_2$ | 406 |
| $SSM_2$ | 107 |

In accord with the present invention, The square roots of the sum of variances without $S_2$ and $S_1$, $SSM_1$, and $SSM_2$ are 9 and 107, respectively. Therefore, $SSM_2$ is greater than $SSM_1$. Hence, the true outlier data point is $S_2$ and this data measurement should be rejected in order to enhance analytical accuracy and precision through error reduction.

Following the above method for rejecting outlier measurements by identifying and rejecting the photometric Signal that forms one of the pair of photometric Signals having the greatest variance between all possible individual mean rates between the totality of multiple photometric Signals and the mean rate of all of the multiple photometric Signals would lead to the identification of an outlier like the ones identified in FIGS. 10 and 11 and encircled by a dashed hexagon, for example.

It will be appreciated by those skilled in that art that a number of variations and enhancements may be made in the above described scheme and still achieve the essence of the present invention. For example, if n is a number much greater than, say ten, both of the above outlier rejection schemes can be repeated several times, each time rejecting a single outlier, resulting in a final set of N mean rates $MR_j$ for n=1 to N, for which $ABS[MR-MR_j]$ are all reasonably similar in magnitude.

For these reasons, the present invention is not limited to those embodiments precisely shown and described in the specification but only by the following claims.

I claim:

1. A method for rejecting outlier measurements in an analytical method having multiple photometric signal values by:

identifying and rejecting the photometric value that forms one of the pair of photometric values having the greatest variance between all possible mean rates between the totality of multiple photometric values and the mean rate of all of the multiple photometric values, wherein said identifying and rejecting comprises:

a) identifying the totality of different pairs of measurement values;

b) calculating rates of data changes for all of said pairs of measurement values;

c) calculating the mean rate of all of the data changes;

d) calculating the variance between the mean rate and the plurality of data changes;

e) identifying the pairs of measurement values having the maximum variance between the mean rate and the plurality of data changes;

f) re-calculating the mean rate of the plurality of data changes, excluding a first one of the two measurement values identified in step e);

g) re-calculating the mean rate of the plurality of data changes, excluding a second one of the two measurement values identified in step e);

h) identifying the absolute values of the differences between the mean rate and the re-calculated mean rates of step f) and step g); and, either, i) rejecting the first one of the two measurement values if the absolute value of the difference between the mean rate and the re-calculated mean rate of step f) is larger than the absolute value of the difference between the mean rate and the re-calculated mean rate of step g), or j) rejecting the second one of the two measurement values if the absolute value of the difference between the mean rate and the re-calculated mean rate of step g) is larger than the absolute value of the difference between the mean rate and the re-calculated mean rate of step f).

2. The method of claim 1 wherein step e) comprises numerically ranking all mean rates from lowest to highest and then repeating steps f) through j) for either one of the lowest or the highest ranked mean rates.

3. The method of claim 1 further comprising repeating steps a) to j) at least once.

* * * * *

UNITED STATES PATENT AND TRADEMARK OFFICE
CERTIFICATE OF CORRECTION

PATENT NO. : 7,039,561 B2 Page 1 of 1
APPLICATION NO. : 10/865,081
DATED : May 2, 2006
INVENTOR(S) : Tie Quan Wei It is certified that error appears in the above-identified patent and that said Letters Patent is hereby corrected as shown below:

Col. 4, line 60, please delete "155" and insert -- 15S --
Col. 4, line 63, please delete "155" and insert -- 15S --
Col. 5, line 11, please delete "90" and insert --9C --

Signed and Sealed this

Fifteenth Day of August, 2006

JON W. DUDAS
*Director of the United States Patent and Trademark Office*